(12) United States Patent
Fatiny (10) Patent No.: US 10,420,627 B2
(45) Date of Patent: Sep. 24, 2019

(54) DENTAL TOOL FOR SHAPING DENTAL RESTORATION

(71) Applicant: King Abdulaziz University, Jeddah (SA)

(72) Inventor: Fahad Ibrahim Fatiny, Jeddah (SA)

(73) Assignee: King Abdulaziz University, Jeddah (SA)

( * ) Notice: Subject to any disclaimer, the term of this patent is extended or adjusted under 35 U.S.C. 154(b) by 37 days.

(21) Appl. No.: 15/454,411

(22) Filed: Mar. 9, 2017

(65) Prior Publication Data
US 2018/0256292 A1 Sep. 13, 2018

(51) Int. Cl.
*A61C 3/08* (2006.01)
*A61C 5/00* (2017.01)

(52) U.S. Cl.
CPC . *A61C 3/08* (2013.01); *A61C 5/00* (2013.01)

(58) Field of Classification Search
CPC ...................................................... A61C 3/08
USPC ...................................................... 433/164
See application file for complete search history.

(56) References Cited

U.S. PATENT DOCUMENTS

| | | |
|---|---|---|
| 691,763 A | 1/1902 | Harper |
| 739,333 A | 9/1903 | Miles |
| 869,035 A | 10/1907 | Wolford |
| 882,711 A | 3/1908 | Pearsall |
| 940,351 A | 11/1909 | Neugebauer |
| 1,209,789 A | 12/1916 | Wilson |
| 1,229,024 A | 6/1917 | Brandt |
| 1,369,582 A | 2/1921 | Wagner |
| 1,382,401 A * | 6/1921 | Zurbrigg .............. A61C 3/08 433/164 |
| 1,402,525 A | 1/1922 | Moseler |
| 1,435,902 A | 11/1922 | Derbyshire |
| 1,455,374 A * | 5/1923 | Ziesel ................. A61C 3/10 30/314 |
| 1,497,749 A * | 6/1924 | Diack ................. A61C 3/08 433/144 |
| 1,691,786 A * | 11/1928 | Roth .................. A61C 3/10 433/143 |
| 1,743,154 A | 1/1930 | Meyer |
| 1,875,680 A | 9/1932 | Van Horn |
| 2,655,726 A | 10/1953 | Diener |
| 2,818,647 A | 1/1958 | Berliner |
| 4,259,069 A | 3/1981 | Lustig |
| 4,270,902 A * | 6/1981 | Wiland ............... A61C 3/10 433/143 |
| 4,586,901 A | 5/1986 | Tanaka et al. |
| 4,643,677 A | 2/1987 | Kim |
| 4,698,019 A * | 10/1987 | Martin ............... A61C 3/10 433/144 |
| 4,747,777 A * | 5/1988 | Ward ................. A61C 5/85 433/141 |

(Continued)

FOREIGN PATENT DOCUMENTS

| | | |
|---|---|---|
| CN | 204636580 U | 9/2015 |
| EP | 0 147 485 A1 | 7/1985 |
| EP | 2 332 485 A1 | 6/2011 |

*Primary Examiner* — Matthew M Nelson
(74) *Attorney, Agent, or Firm* — Oblon, McClelland, Maier & Neustadt, L.L.P.

(57) ABSTRACT

A dental instrument for shaping a dental restoration. The instrument includes an end with at least one undulating edge which eases the placement, manipulation, and sculpting of dental restoration.

18 Claims, 13 Drawing Sheets

(56) References Cited

U.S. PATENT DOCUMENTS

| | | | | |
|---|---|---|---|---|
| 5,080,588 A * | 1/1992 | O'Brien | ............ | A61C 3/02 433/165 |
| 5,098,292 A * | 3/1992 | Lazarof | ............ | A61C 5/50 433/141 |
| 5,788,499 A | 8/1998 | Hoffman | | |
| 6,099,310 A | 8/2000 | Bornstein et al. | | |
| 6,206,698 B1 * | 3/2001 | Billingsley | ............ | A61C 3/08 433/164 |
| D442,690 S * | 5/2001 | Fischer | ............ | A61C 3/10 D24/152 |
| 6,257,885 B1 | 7/2001 | Säfström | | |
| 6,705,865 B1 * | 3/2004 | Szymaitis | ............ | A61C 3/00 433/141 |
| 8,057,231 B2 | 11/2011 | Viscomi | | |
| 8,297,972 B2 * | 10/2012 | Gordon | ............ | A61B 13/00 433/140 |
| D728,788 S * | 5/2015 | Chu | ............ | A61C 3/10 D24/152 |
| 2005/0095558 A1 * | 5/2005 | Jones | ............ | A61C 3/00 433/144 |
| 2005/0100860 A1 | 5/2005 | Kameli | | |
| 2005/0130099 A1 * | 6/2005 | Besek | ............ | A61C 3/08 433/80 |
| 2005/0202373 A1 | 9/2005 | Peng et al. | | |
| 2007/0212660 A1 * | 9/2007 | Rueggeberg | ............ | A61C 1/07 433/32 |
| 2008/0014553 A1 | 1/2008 | Garrison et al. | | |
| 2009/0042165 A1 | 2/2009 | Garrison et al. | | |
| 2010/0143866 A1 * | 6/2010 | Lasner | ............ | A61C 3/14 433/144 |
| 2012/0301848 A1 * | 11/2012 | O'Donnell | ............ | A61C 5/50 433/164 |
| 2014/0199660 A1 * | 7/2014 | Viscomi | ............ | A61C 3/08 433/226 |

* cited by examiner

DENTAL TOOL FOR SHAPING DENTAL RESTORATION

BACKGROUND OF THE INVENTION

Field of the Invention

This disclosure relates to a dental instrument that is designed to shape a dental restoration on a tooth. The dental instrument may also be useful for removing excess dental restoration from the occlusal, labial, and interproximal surfaces of a tooth.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Dental composites have distinct intrinsic properties from traditional amalgam (mercury based) restorations. In particular, composites with a stickiness quality undesirably adhere to traditional instruments during the handling of composites in various procedures. This adherence interferes with the release of the instrument upon withdrawing from the site of administration. Hence pull-back of the adhering composite makes it difficult to properly insert and adapt the composite to the prepared tooth. Further, the displacement, rather than the compaction, of the composite renders traditional instruments ineffective during the adaptive process.

After the cavity is filled with the composite, it is cured, or hardened, by subjecting it to ultraviolet light. Subsequently, the excess composite is removed by scraping, or carving, it away from the tooth.

When removing excess composite, it is important to carefully remove all of the excess, particularly along the gum line and between the teeth. Any excess composite remaining on a tooth after a filling is formed can trap food particles or cause discomfort to the patient. However, removing excess composite is difficult due to its hardness and a lack of dental instruments designed specifically for this task.

Currently, excess composite is typically removed from a tooth with the aid of an instrument designed for another purpose such as an instrument for removing plaque having a cylindrical handle with a pick at one end or an instrument for handling amalgam having a single blade extending from a cylindrical handle. But neither of these types of instruments is well suited for use in removing excess composite from interproximal surfaces of a tooth.

Therefore, there exists a need for improvements in dental instruments of the type used for shaping and removing excess dental restoration from a prepared tooth. The present disclosure fulfills this need and provides further related advantages.

SUMMARY OF THE DISCLOSURE

The foregoing description is intended to provide a general introduction and summary of the present disclosure and is not intended to be limiting in its disclosure unless otherwise explicitly stated. The various embodiments, together with further advantages, will be best understood by reference to the following detailed description taken in conjunction with the accompanying drawings.

A first aspect of the disclosure relates to a dental tool, comprising: (i) a first working end member, a second working end member, and a handle therebetween, wherein each working end member is connected to the handle and comprises: (i) a curved section connected to the handle and disposed at a first acute angle to a longitudinal axis of the handle; and (ii) an end in a shape of a cruciform connected to the curved section, wherein the end comprises at least one undulating edge; where a first diagonal connecting a first corner of the cruciform to the curved section is disposed at a second acute angle to the longitudinal axis of the handle, and both working end members and the handle form a unitary construction.

In one embodiment, the at least one undulating edge is serrated.

In one embodiment, the undulating edge is serrated with a plurality of serrations, and each serration has a width in a range of 0.01-2 mm.

In one embodiment, a concave portion of the at least one, undulating edge is in a shape of an arc with a radius of curvature in a range of 0.5-15 mm.

In one embodiment, the arc has an arc length in a range of 1-12 mm.

In one embodiment, the arc has a chord length in a range of 0.5-10 mm.

In one embodiment, the end in the shape of a cruciform comprises 3-6 undulating edges.

In one embodiment, the end comprises 4 undulating edges.

In one embodiment, a length of the first diagonal is in a range of 1-4 times a length of a second diagonal which connects a second corner of the cruciform to a third corner of the cruciform.

In one embodiment, the length of the first diagonal is in a range of 1-3 times the length of the second diagonal.

In one embodiment, the end of the first working end member lies in a first plane, the end of the second working end member lies in a second plane, and the first plane is perpendicular or substantially perpendicular to the second plane.

In one embodiment, each end has a thickness in a range of 0.1-4 mm.

In one embodiment, a top face of each end is flat.

In one embodiment, a bottom face of each end is flat.

In one embodiment, each end is coated with at least one non-stick material selected from the group consisting of polytetrafluoroethylene, titanium nitride and a chemical vapor deposited polyp-xylylene polymer.

In one embodiment, the first acute angle is in a range of 5-60°.

In one embodiment, the second acute angle is in a range of 5-60°.

In one embodiment the handle is knurled.

A second aspect of the disclosure relates to a method for restoring a tooth, comprising: (i) filling a tooth cavity with a dental restoration (ii) compressing and/or distributing the dental restoration with the dental tool of the first aspect thereby shaping the dental restoration to conform to a shape of the tooth; and (iii) removing excess dental restoration.

In one embodiment, the dental restoration is an uncured composite resin.

DETAILED DESCRIPTION OF THE DISCLOSURE

Embodiments of the present disclosure will now be described more fully hereinafter with reference to the accompanying drawings, in which some, but not all embodiments of the disclosure are shown.

FIGS. 1-5 show several embodiments of the dental tool. The first aspect of the disclosure relates to a dental tool comprising: (i) a first working end member 101, (ii) a second working end member 102, and (iii) a handle 103 therebetween, wherein each working, end member 101/102 is connected to the handle 103 and comprises: (iv) a curved section 104 connected to the handle 103 and disposed at a first acute angle, α, to a longitudinal axis of the handle 103, and (v) an end 105 in a shape of a cruciform connected to the curved section 104, where the end 105 comprises at least one undulating edge 106. A first diagonal connecting a first corner 107 of the cruciform to the curved section 104 is disposed at a second acute angle, β, to the longitudinal axis of the handle 103, and both working end members and the handle 103 form a unitary construction (see FIG. 5).

The dental tool may be made of an autoclavable material such as stainless steel, cobalt-chromium alloy, titanium, titanium-based alloy, polymer (e.g., dimethicone, methicone, phenyl trimethicone, cyclomethicone, polytetrafluoroethylene, expanded polytetrafluoroethylene, fluorinated ethylene propylene, perfluoroalkoxy, poly vinylidene fluoride, Parylene N, Parylene C, Parylene D, THV terpolymer, and copolymers thereof), and mixtures thereof. When in contact with the dental restoration the materials described herein may not discolor the dental restoration. Preferably, at least a portion of the dental tool is made of stainless steel. In one embodiment, the entire dental tool is made of a rigid, non-metallic material, such as one or more of the aforementioned polymers, to avoid scratching or otherwise causing damage to dental implant abutments, attachments, fixtures, or other metallic features in an oral cavity. The potential for infection and related damage to gingival tissue, bone, and surrounding teeth may also be minimized. The use of a rigid material provides improved tactile sensitivity. Further, the use of the non-metallic material also minimizes costs related to production and replacement of the dental tool. A non-metallic dental tool is also lighter than a metallic dental tool.

Figure 3:
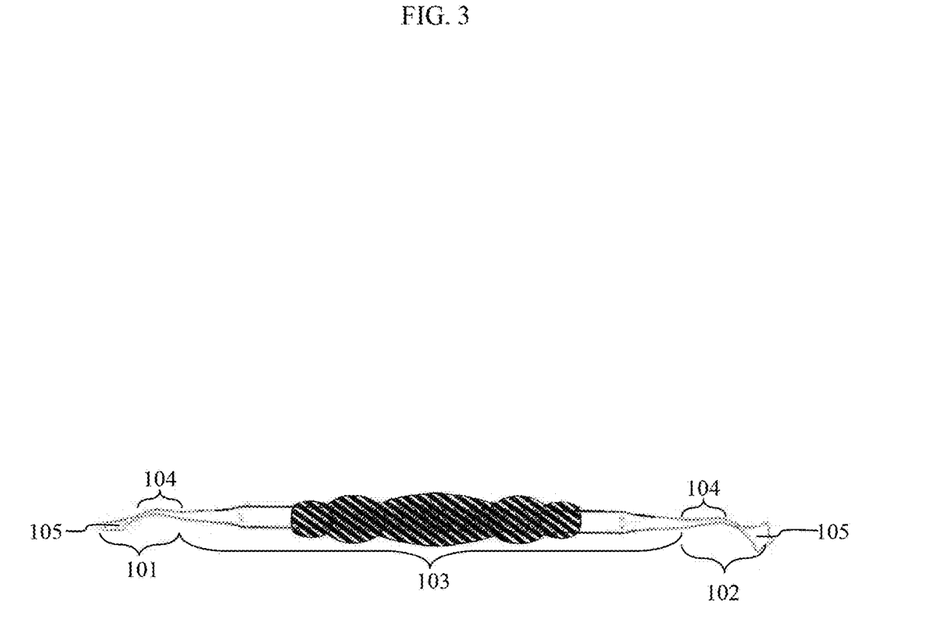
FIG. 3 shows a perspective view of another embodiment of the dental tool.
Figure 4:
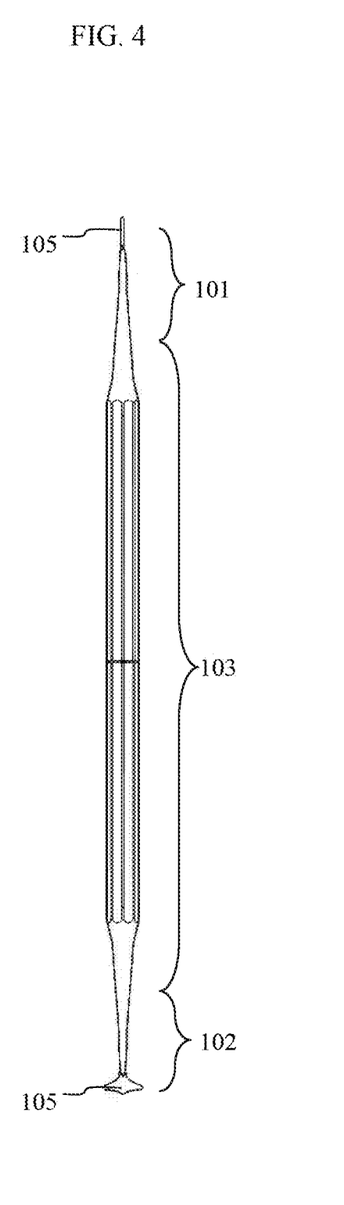
FIG. 4 shows a side view of another embodiment of the dental tool.
Figure 5:
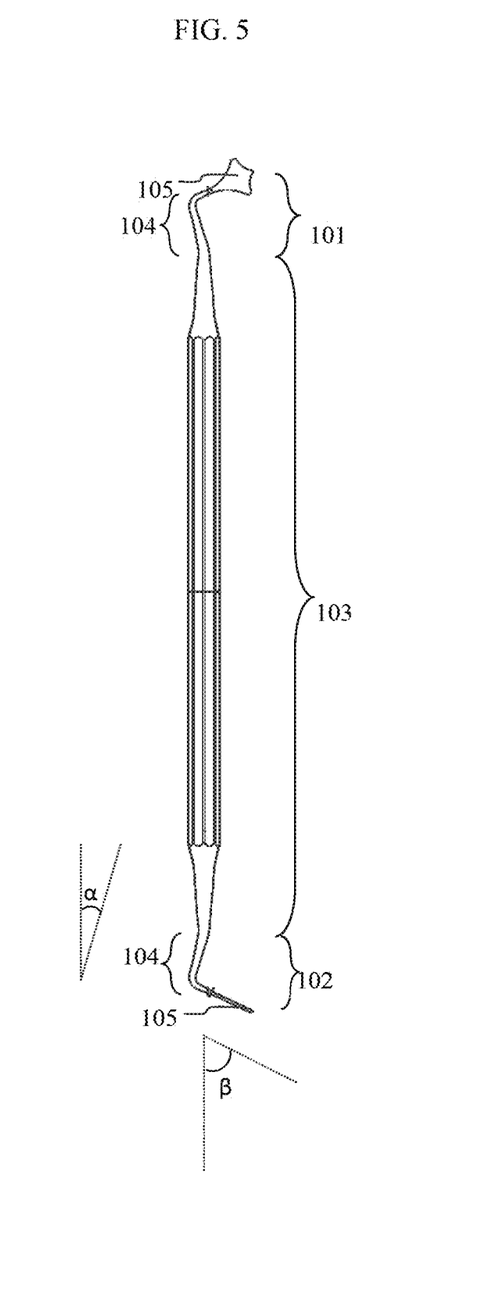
FIG. 5 shows another side view of the dental tool in FIG. 4.
Figure 6:
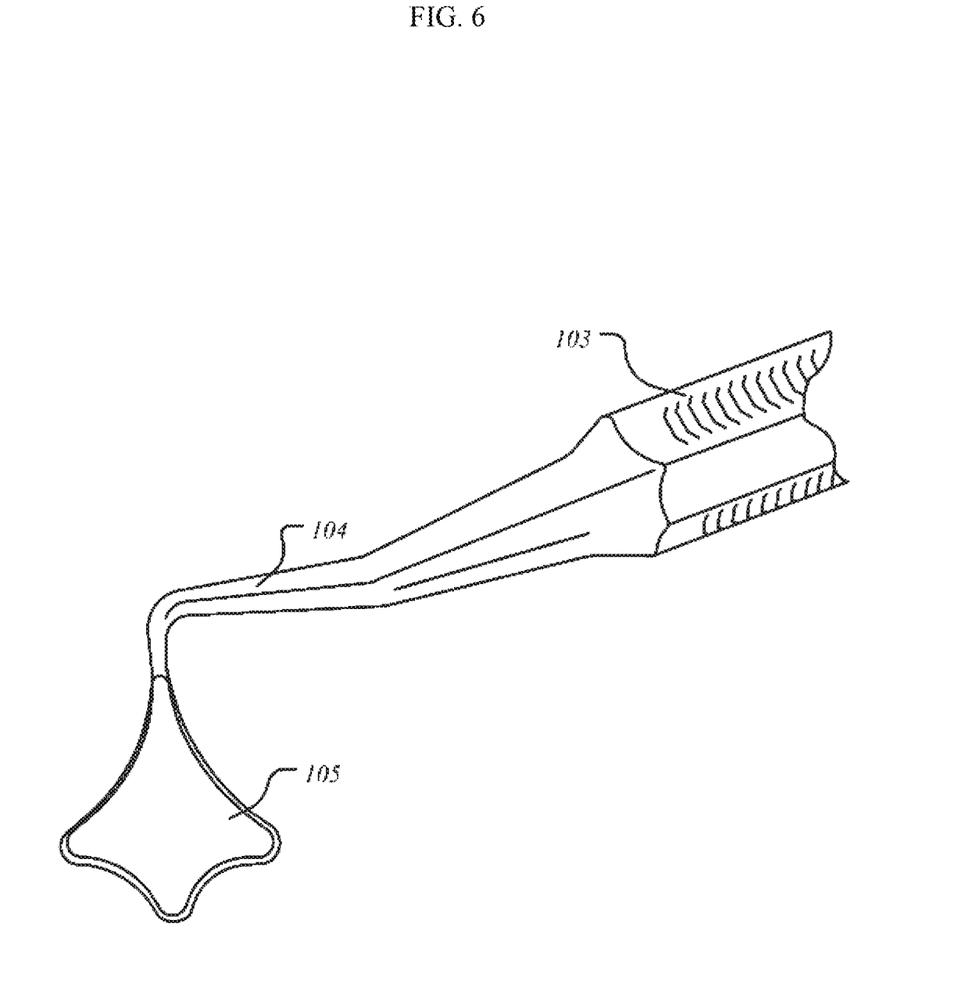
FIG. 6 shows an enlarged view of a working end member of the embodiment of the dental tool shown in FIG. 2.
Figure 7:
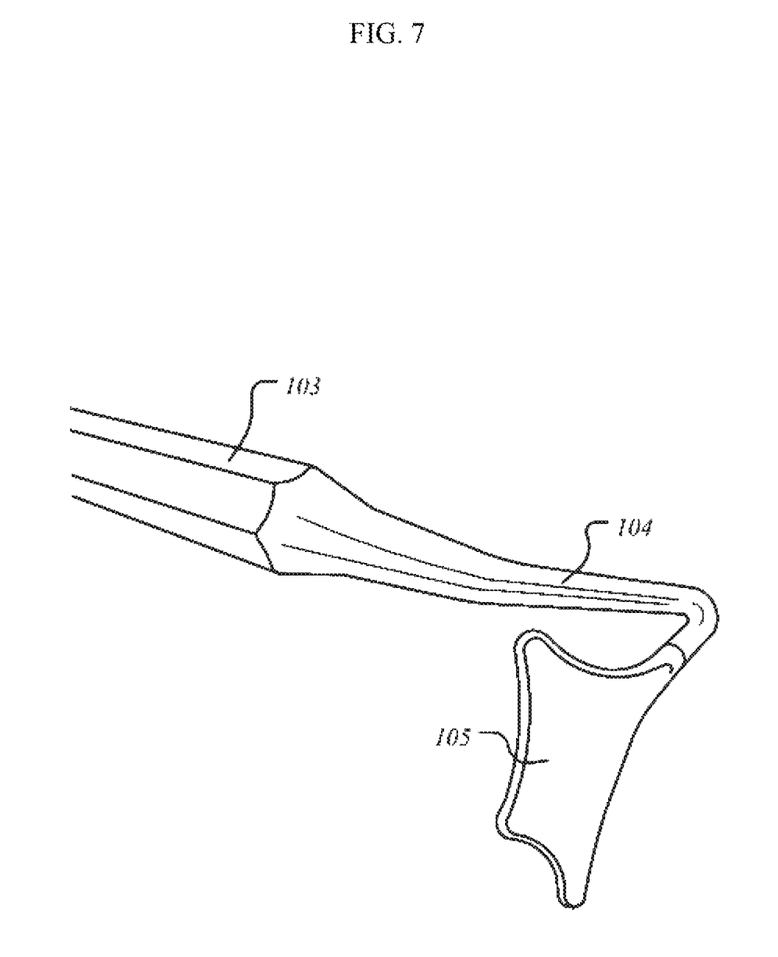
FIG. 7 shows an enlarged view of a working end member of the embodiment of the dental tool shown in FIG. 1.

The handle 103 is elongated and sized for manipulation by hand into a patient's mouth. The handle 103 may be of any length (e.g. 50-200 min, preferably 50-150 mm, more preferably 100-150 mm) and any diameter (e.g. 1-10 mm, preferably 2-7 mm, more preferably 4-7 mm). A cross section of the handle 103 may be a circle, an oval, or a polygon (e.g., triangle, hexagon, rhombus, trapezium, parallelogram, pentagon, heptagon, octagon, nonagon, decagon, undecagon, and dodecagon). The polygon may be regular (i.e. all sides equal in length and all equal angles), irregular, convex (i.e. no internal angle is more than 180°), or concave. The term "diameter" refers to the greatest possible distance measured from one point on the perimeter of the cross section through the center of the cross section to a point directly across from it. The handle 103 may include one or more regions having varying thickness, knurled patterns, or other materials (e.g. a rubber sleeve) to provide a good grip for the dental practitioner. In one embodiment, the handle 103 has a hexagonal cross section and at least one face of the hexagon has a knurled pattern which covers the entire length of the face (e.g., FIGS. 2 and 6). The knurled pattern may be an angled pattern, a diamond pattern, or a straight pattern (e.g., axially or circumferentially), preferably a diamond pattern. In one embodiment, the knurled pattern is a straight pattern and a distance between each line may be at least 0.05 mm, at least 0.1 mm, or at least 0.15 mm, and up to 0.3 mm, up to 0.25 mm, or up to 0.2 mm. In some embodiments, the handle 103 has a rubber sleeve. Exemplary types of rubber include, without limitation, natural rubber and synthetic rubber such as neoprene rubber, silicone rubber. EPDM rubber, vinyl rubber, nitrile rubber, butyl rubber, and hypalon rubber. The sleeve may have a shape of a hollow cylinder. In another embodiment, the handle 103 is formed with a series of convex and mutually adjacent knobs disposed axially therealong and surrounding the middle of the handle 103 (e.g., as shown in FIG. 3). Each of the knobs has a circular cross section that is larger than the diameter of the handle 103. For example, the diameter of the knob is at most 10 mm larger, preferably at most 7 mm larger, more preferably at most 5 mm larger than the diameter of the handle 103. The knobs may be of the same diameter or increase in diameter from the first knob adjacent each working end member of the dental tool to a medial largest diameter knob. For example, the medial largest diameter knob may have a diameter that is at most 7 mm larger, preferably at most 5 mm larger, more preferably at most 2 mm larger than the diameter of the first knob.

The curved section 104 is disposed at a first acute angle, a, relative to the longitudinal axis of the handle 103. This orientation facilitates the access of the dental tool to the dental restoration. The first acute angle may be in a range of 5-60°, preferably 15-50°, more preferably 35-50°. Each of the first acute angle of the first and second working end members may be the same or different to enable access to different portions of the oral cavity. For example, the first acute angle of the first working end member 101 may be smaller than that of the second working end member 102 by at most 15°, preferably at most 10°, more preferably at most 5°. The second acute angle, β, may be in a range of 5-60°, preferably 15-50°, more preferably 35-50°. In other embodiments, β may be larger than 60°, larger than 65°, or larger than 70°, and less than 90°, less than 80°, or less than 75°. In one embodiment, β is 90°. Each second acute angle of the first and second working end member may be the same or different to enable access to different portions of the tooth.

For example, the second acute angle of the first working end member 101 may be smaller than that of the second working end member 102 by at most 15°, preferably at most 10°, more preferably at most 5°. In one embodiment, the first acute angle is larger than the second acute angle by at most 45°, preferably at most 30°, more preferably at most 15°. In another embodiment, the first acute angle is smaller than the second acute angle by at most 45°, preferably at most 30°, more preferably at most 15°.

In an embodiment, the curved section 104 has a diameter smaller than that of the handle 103, for facilitating access and maneuverability within the patient's mouth. For example, the diameter of the curved section 104 may be in a range of 0.5-9 mm, preferably 1-5 mm, more preferably 1-3 mm. In one embodiment, the diameter of the curved section 104 is uniform throughout the curved section 104. In another embodiment, the diameter of the curved section 104 tapers from a largest diameter at the connection to the handle 103 to a smallest diameter at the connection to the end 105. For example, the largest diameter is at most 8 mm, preferably at most 6 mm, more preferably at most 3 mm larger than the smallest diameter of the curved section 104. A length of the curved section 104 may be in a range of 5-20 mm, preferably 5-15 mm, more preferably 7-12 mm. Each of the curved section 104 of the first and second working end member may have the same length or different lengths to enable access to different portions of the tooth. For example, the curved section 104 of the first working end member 101 may be at most 10 mm longer, preferably at most 5 mm longer, more preferably at most 3 mm longer than the curved section 104 of the second working end member 102.

Figure 8:
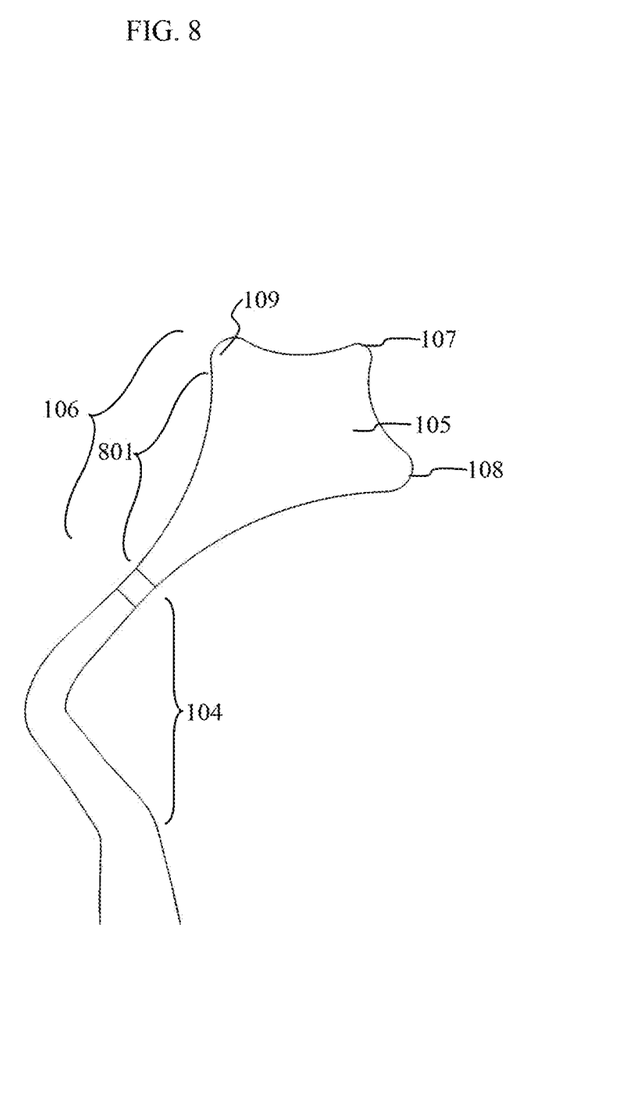
FIG. 8 shows a top view of the working end member.

FIGS. 6-9 show a close-up view of the ends 105 of the dental tool. The end 105 in the shape of a cruciform may comprise 3-6 undulating edges, 3-5 undulating edges, or 4 undulating edges. As used herein, an undulating edge 106 refers to a wave-like edge containing a crest and a trough. The undulating edge 106 has a concave portion 801 (e.g., as shown in FIG. 8) which may be in a shape of an arc with a radius of curvature in a range of 0.5-15 mm, 1-12 mm, or 1-7 mm. The arc may have an arc length in a range of 1-12 mm, 2-10 mm, or 2-8 mm. The arc may have a chord length in a range of 0.5-10 mm, 1-8 mm, or 1-5 mm.

Figure 9:
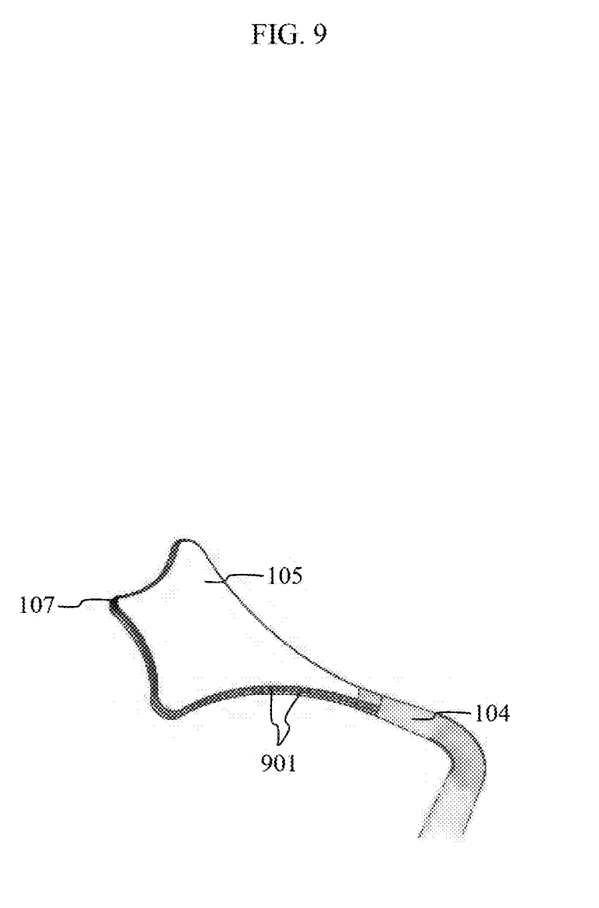
FIG. 9 shows a perspective view of a serrated undulating edge.
Figure 10:
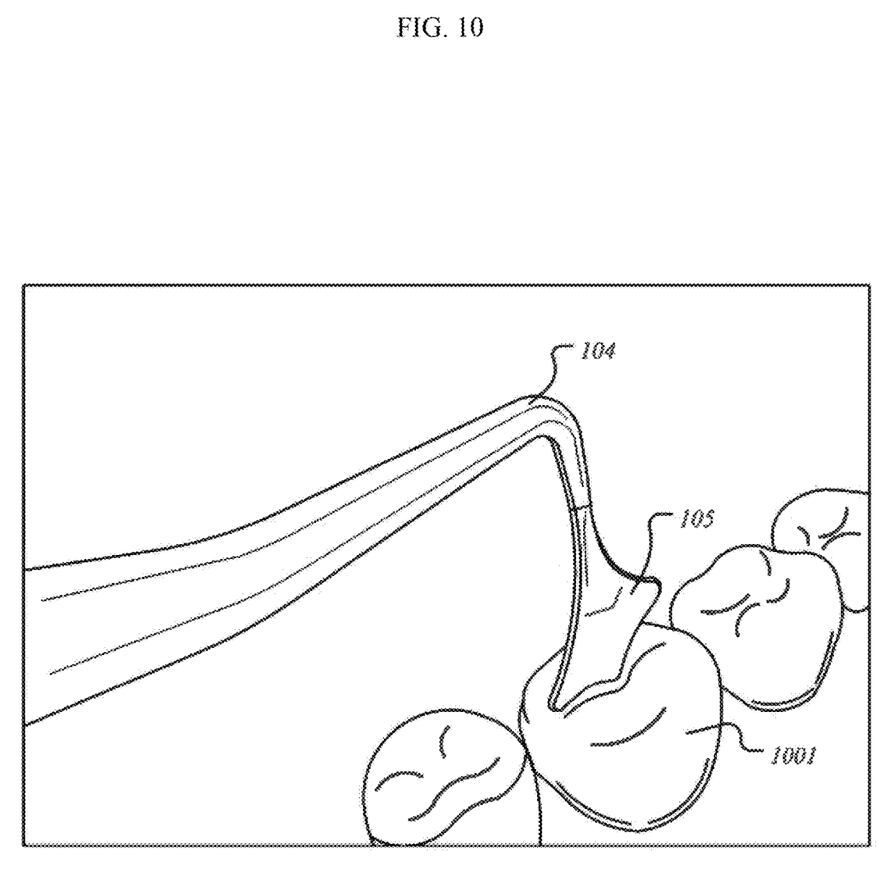
FIG. 10 shows a perspective view of an embodiment of the end and a tooth.
Figure 11:
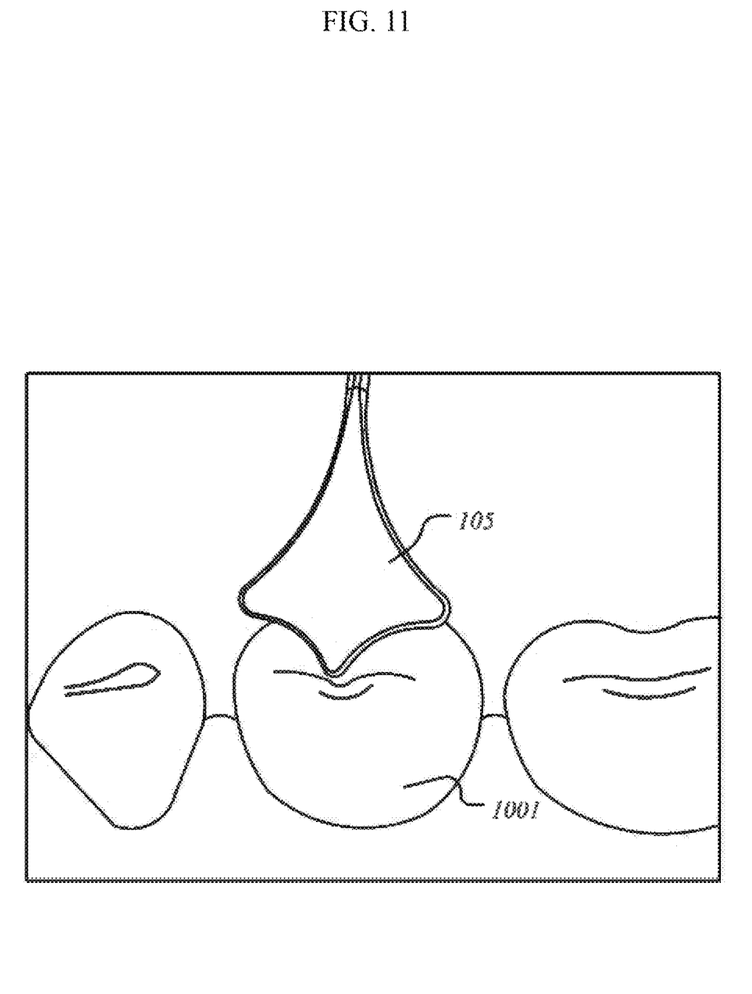
FIG. 11 shows another perspective view of the embodiment of the end and the tooth in FIG. 10.
Figure 12:
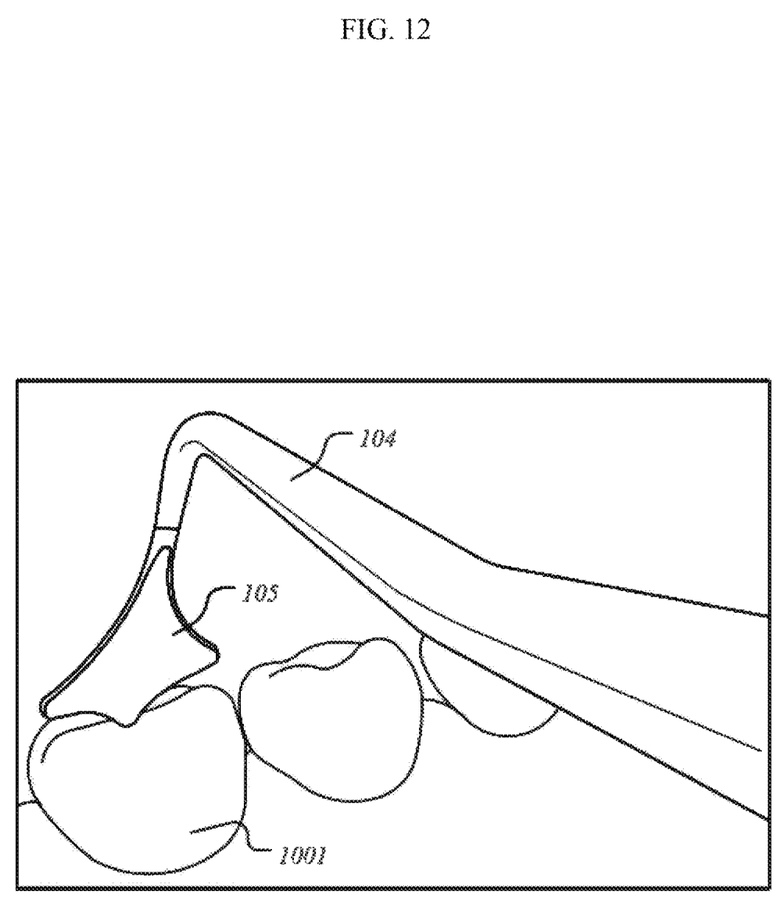
FIG. 12 shows a perspective view of an embodiment of the end and a tooth.
Figure 13:
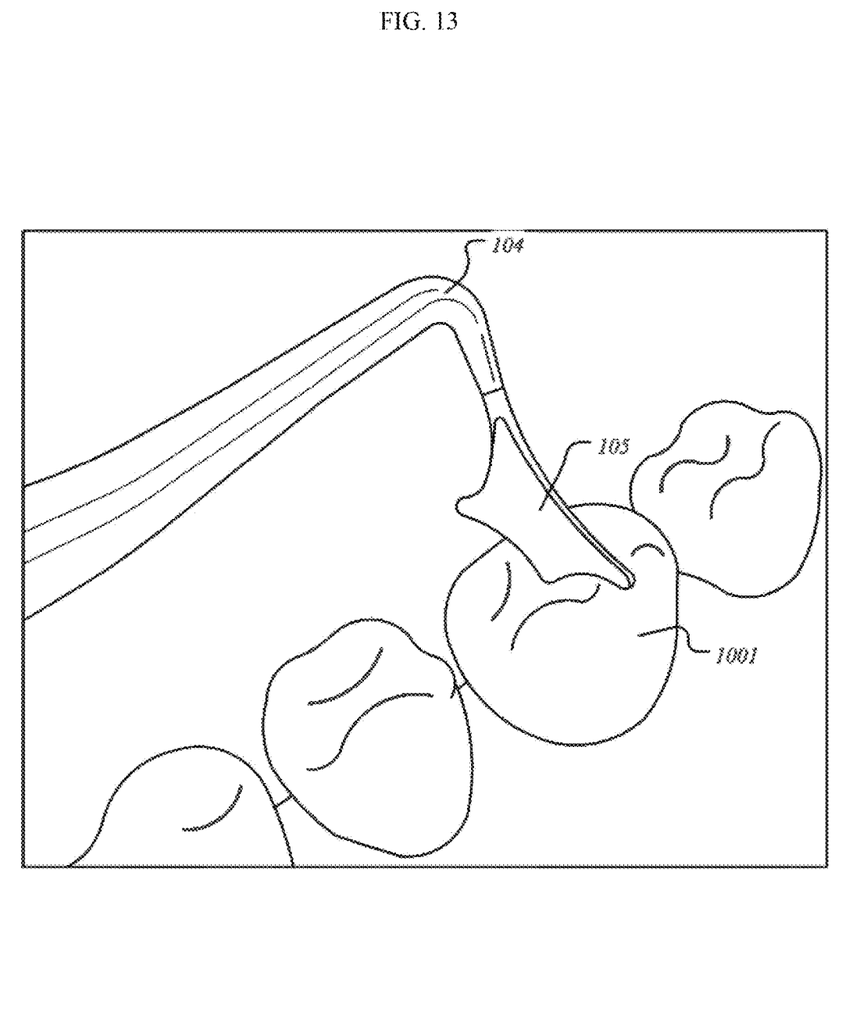
FIG. 13 shows a perspective view of the embodiment of the end in FIG. 12 and a tooth.

In one embodiment, the at least one undulating edge 106 is not serrated. In some embodiments, the at least one undulating edge 106 is serrated (e.g., as shown in FIG. 9). The serrated undulating edge 106 comprises a plurality of serrations 901. The plurality of serrations 901 may be located only in the concave portion 801 of the undulating edge 106. In other embodiments, the serrations may be located in the trough or peak sections of the cruciform section of the undulating edge 106. The serration may be partial, for example beginning at one half the peak to trough height with serrations at the trough or at the peak. Each serration 901 may have a curved edge, which may be recessed or protruding. The different types of serrations may be useful for sculpting the secondary and tertiary anatomy into the dental restoration. The at least one undulating edge 106 may have recessed serrations, protruding serrations, or both. In the cruciform which comprises more than one serrated undulating edges, at least one serrated undulating edge 106 may have a plurality of recessed serrations while the remaining serrated undulating edge(s) has a plurality of protruding serrations. A width of the serration 901, measured from both ends of the curved edge, may be in a range of 0.01-2 mm, 0.01-1.5 mm, 0.01-1 mm, 0.01-0.5 mm, or 0.01-0.1 mm. The plurality of serrations may have uniform or varied widths. For example, a largest width of the serration 901 may be at least 5%, 10%, 20%, or 30%, and at most 100%, at most 90%, at most 80%, at most 70%, or at most 60% wider than a smallest width of the serration 901. In some embodiments, the largest width may be at least 5%, 10%, or 15%, and at most 40%, at most 30%, or at most 20% wider than an average width of the plurality of serrations 901, which may be in a range of 0.01-1 mm, 0.01-0.5 mm, or 0.01-0.1 mm. A depth of each serration 901 may be in a range of 0.01-2 mm, 0.01-1 mm, or 0.01-0.5 mm. The plurality of serrations 901 may have uniform or varied depths. For example, a largest depth of the serration 901 may be at least 5%, 10%, 20%, or 30%, and at most 100%, at most 90%, at most 80%, at most 70%, or at most 60% wider than a smallest depth of the serration 901. In some embodiments, the largest depth may be at least 5%, 10%, or 15%, and at most 40%, at most 30%, or at most 20% wider than an average depth of the plurality of serrations 901, which may be in a range of 0.01-1 mm, 0.01-0.5 mm, or 0.01-0.1 mm.

Each of the first corner 107, the second corner 108, and the third corner 109 may be independently round, blunt, or sharp. Each end 105 may have a mix of round, blunt, and sharp corners. The round corner may be useful for removing excess dental restoration from the tooth and a sharp corner may be useful for sculpting secondary and tertiary anatomy into the dental restoration.

In one embodiment, the dental tool has four undulating edges. In this embodiment, a length of the first diagonal, which is a line connecting the first corner 107 to the connection to the curved section 104, may be at least 1 mm, at least 2 mm, at least 3 mm, at least 4 mm, or at least 5 min, and up to 15 min, up to 12 min, up to 10 mm, or up to 8 mm. A length of the second diagonal, which is a line connecting a second corner 108 of the cruciform to a third corner 109 of the cruciform, may be at least at least 1 mm, at least 2 mm, at least 3 mm, at least 4 mm, or at least 5 mm, and up to 15 mm, up to 12 mm, up to 10 mm, or up to 8 mm. As used herein, an "aspect ratio" of the cruciform refers to the length of the first diagonal to the length of the second diagonal. The aspect ratio may be at least 1:1, at least 1:2, at least 1:3, or at least 1:4, and up to 15:1, up to 10:1, up to 1:6, or up to 5:1.

In the embodiment of the dental tool with four undulating edges, the first diagonal intersects the second diagonal. A straight line distance from the point of intersection to the first corner 107 may be at least 0.3 mm, at least 0.8 mm, at least 1 mm, at least 2 mm, at least 3 mm, at least 4 mm, or at least 5 mm, and up to 13 mm, up to 11 mm, up to 9 mm, or up to 7 mm. A straight kine distance from the point of intersection to the second corner may be at least 0.3 mm, at least 0.8 mm, at least 1 mm, at least 2 mm, at least 3 mm, at least 4 mm, or at least 5 mm, and up to 13 mm, up to 11 mm, up to 9 mm, or up to 7 mm. An acute angle between the first diagonal and the second diagonal may be at least 10°, at least 20°, at least 30°, at least 40°, or at least 50°, and less than 90°, up to 85°, up to 80°, up to 75°, or up to 70°. In some embodiments, the first diagonal intersects the second diagonal at right angles. The first diagonal may bisect the second diagonal. The cruciform may be symmetrical (i.e., the first diagonal is a line of symmetry) or asymmetrical (i.e., there is no line of symmetry in the cruciform).

The end 105 of the first working end member 101 lies in a first plane, and the end 105 of the second working end member 102 lies in a second plane. The first plane may be parallel or substantially parallel to a longitudinal axis of the handle 103. As used herein, the term "substantially parallel" refers to the first plane being aligned at no tore than 10°, no more than 7°, no more than 5°, no more than 3°, or no more than 1°, relative to the longitudinal axis of the handle 103. The first plane may be perpendicular or substantially perpendicular to the second plane. As used herein, the term "substantially perpendicular" refers to the first plane is aligned at no more than 10°, no more than 7° no more than 5° no more than 3°, or no more than 1°, relative to the second plane.

A top face, a bottom face, or both of each end 105 may be flat or curved. Each end 105 may have a uniform thickness that is in a range of 0.1-4 mm, preferably 0.1-2 mm, more preferably 0.1-1 mm. In some embodiments, the end 105 tapers in thickness from the point where it connects to the curved section 104 to the first corner 107. The thickness at the connection at the curved section 104 may be in a range of 1-4 mm, preferably 1-3 mm, more preferably 1-2 mm. The thickness at the corner 107 may be in a range of 0.1-3.5 mm, preferably 0.1-2.5 mm, more preferably 0.1-1 mm.

Each end 105 may be coated with a non-stick material. Exemplary non-stick materials include, without limitation, polymers (e.g., dimethicone, methicone, phenyl trimethicone, cyclomethicone, polytetrafluoroethylene, expanded polytetrafluoroethylene, fluorinated ethylene propylene, perfluoroalkoxy, polyvinylidene fluoride, Parylene™ N, Parylene™ C, Parvlene™ D, TFIV terpolymer, and copolymers thereof), ceramics (e.g., silica, titanium nitride, titanium oxide), and combinations thereof. As used herein, the chemical vapor deposited polyp-xylylene) polymer refers to Parylene™ N, Parylene™ C, Parylene™ D, and combinations thereof. The presence of the non-stick material makes the dental tool resists adherin to dental restoration.

An average roughness ($R_a$) of the non-stick material is less than 2.5 μm, less than 2 μm, less than 1.5 μm, less than 1 μm, or less than 0.5 μm. A coefficient of static friction, coefficient of kinetic friction, or both, of the non-stick material may be less than 0.30, less than 0.25, less than 0.20, less than 0.15, or less than 0.10, and more than 0. The coefficient of static friction refers to the friction force between two objects when neither of the objects is moving. The coefficient of kinetic friction is the force between two objects when one object is moving, or if two objects are moving against each other. The coefficient of friction is usually between 0 and 1 but can be greater than 1. A value of 0 means there no fiction between the objects.

In some embodiments, each end 105 is made from the metals described herein and the non-stick material may be coated on each end. A thickness of the coating may be at least 0.1 μm, at least 0.5 μm, at least 1 μm, at least 10 μm, at least 50 μm, at least 100 μm, or at least 200 μm, and up to 3.500 μm, up to 3,000 μm, up to 2,000 μm, up to 1,500 μm, or up to 1,000 μm.

The ends may be coated with at least one polymer by vacuum deposition. The ends are exposed to gas-phase monomers at a low pressure (e.g., less than 1 bar, less than 0.5 bar, less than 0.1 bar, less than 0.05 bar, or less than 0.01 bar, and more than 0 bar) and a temperature in a range of 10-40° C., 15-35° C., or 20-30° C. The polymer condenses on the ends thereby forming a coating of non-stick material.

Figure 1:
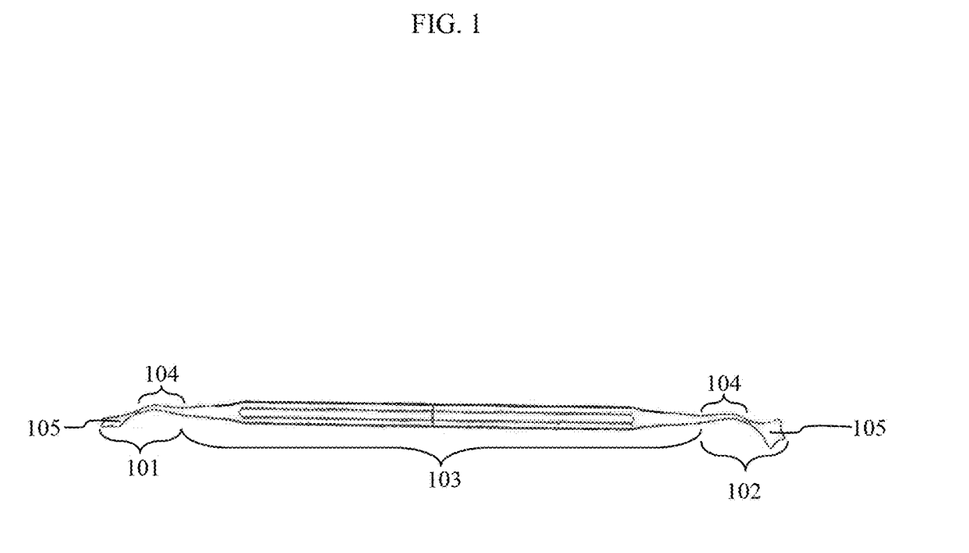
FIG. 1 shows a perspective view of an embodiment of the dental tool.
Figure 2:
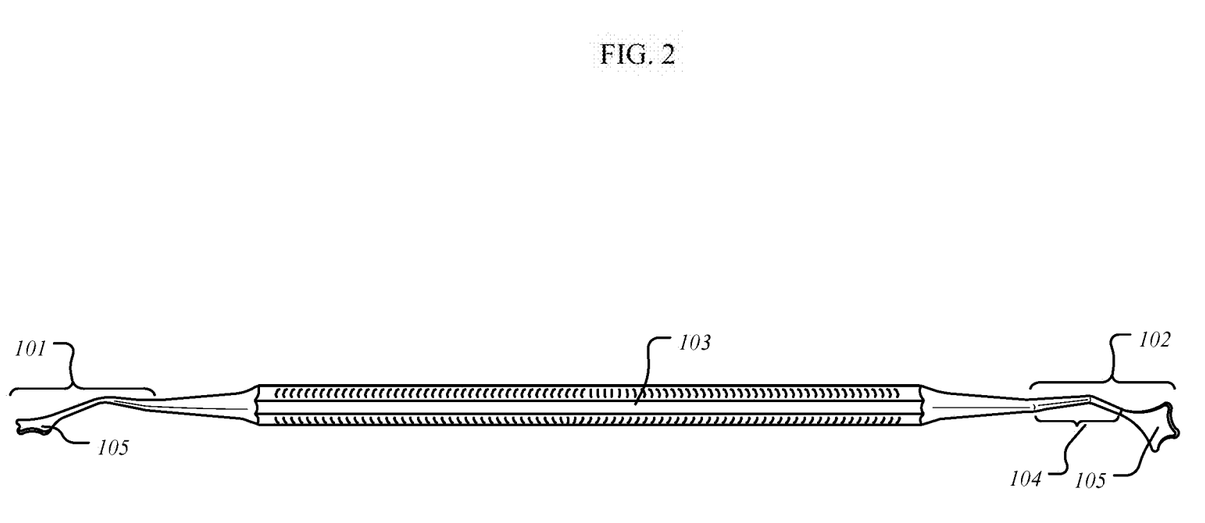
FIG. 2 shows a perspective view of another embodiment of the dental tool.

While the dental tools of FIGS. 1 and 3 have been illustrated with opposite ends 105 of identical configuration, a dental tool with ends in different configurations may be useful for shaping the composite in two different types of teeth. For example, a dental tool may comprise an end 105 designed for pre-molars and/or molars and another end 105 designed for incisors and/or canines.

Further, while the curved sections 104, the ends 105, and the handle 103 have been illustrated and described as unitary, these individual elements may be discrete and fastened together in any suitable manner, such as snap-fitting, force-fitting, adhesives, fasteners, and exterior threads for engagement with complementary interior threads within an end 105 of the handle 103. In another embodiment, the end 105 may be made entirely of a non-stick material, which may be different from the material of the curved section 104 and the handle 103, and the end 105 comprises exterior threads for engagement with complementary interior threads within an end of the curved section 104.

The second aspect of the disclosure relates to a method for restoring a tooth 1001, which has a Class I caries, a Class II caries, a Class III caries, a Class IV caries, a Class V caries, and/or a Class VI caries. The tooth 1001 may have a cavity and/or cracks. In some embodiments, the tooth 1001 is broken or worn down from misuse (such as from nail-biting or tooth grinding).

The tooth 1001 may be restored by filling with dental restoration, which may be injected into the cavities or applied with the dental tool and then compacts the material to fill the cavities. Dental restorations compatible with this method include, without limitation, composite resin, glass ionomer, and combinations thereof.

FIGS. 10-13 show that both working ends may be useful for shaping dental restorations in a posterior tooth 1001 (e.g. premolars and molars) in the oral cavity.

This shape allows the operator to distribute, compress, shape, and manipulate uncured dental restoration on the occlusal surface of posterior teeth. It also helps to faun the grooves and ridges typically found on upper and lower posterior teeth. In addition it assists in removing excess dental restoration.

The ends may also be useful for dental restorations on the anterior teeth (e.g., incisors and canines) in the oral cavity. For example, by placing one of the ends on the cervical part of the anterior tooth and moving the end 105 to the incisal edges the uncured dental restoration may be shaped to form the crest of curvature of the tooth. Pressing the flat surface of the end 105 onto the dental restoration will form the flat surface of the labial of anterior teeth. This working end 105 also shapes and forms the mesial and distal labial ridges of anterior teeth by also moving one of the undulating edges from the cervical to the incisal edge of anterior teeth. Also, the end 105 can also be used to remove excess dental restoration from the mesial and distal contacts of anterior teeth.

The invention claimed is:

1. A dental tool, comprising:
   a first working end member, a second working end member, and a handle therebetween, wherein each working end member is connected to the handle and comprises:
   a curved section connected to the handle and disposed at a first acute angle to a longitudinal axis of the handle; and
   an end in a shape of a cruciform connected to the curved section, wherein the end comprises four undulating edges connected smoothly with each other;
   wherein a first diagonal connecting a first corner of the cruciform to the curved section is disposed at a second acute angle to the longitudinal axis of the handle, and both working end members and the handle form a unitary construction, and wherein a length of the first diagonal is in a range of 1-4 times a length of a second diagonal which connects a second corner of the cruciform to a third corner of the cruciform, wherein the first corner, the second corner, and the third corner are round, wherein a top face and a bottom face of each end is flat.

2. The dental tool of claim 1, wherein at least one undulating edge is serrated.

3. The dental tool of claim 2, wherein the at least one undulating edge is serrated with a plurality of serrations, and each serration has a width in a range of 0.01-2 mm.

4. The dental tool of claim 1, wherein a concave portion of at least one undulating edge is in a shape of an arc with a radius of curvature in a range of 0.5-15 mm.

5. The dental tool of claim 4, wherein the arc has an arc length in a range of 1-12 mm.

6. The dental tool of claim 4, wherein the arc has a chord length in a range of 0.5-10 mm.

7. The dental tool of claim 1, wherein the length of the first diagonal is in a range of 1-3 times the length of the second diagonal.

8. The dental tool of claim 1, wherein the end of the first working end member lies in a first plane, the end of the second working end member lies in a second plane, and the first plane is perpendicular or substantially perpendicular to the second plane.

9. The dental tool of claim 1, wherein each end has a thickness in a range of 0.1-4 mm.

10. The dental tool of claim 1, wherein each end is coated with at least one non-stick material selected from the group consisting of polytetrafluoroethylene, titanium nitride, and a chemical vapor deposited poly(p-xylylene) polymer.

11. The dental tool of claim 1, wherein the first acute angle is in a range of 5-60°.

12. The dental tool of claim 1, wherein the second acute angle is in a range of 5-60°.

13. The dental tool of claim 1, wherein the handle is knurled.

14. The dental tool of claim 1, wherein each end has a uniform thickness.

15. The dental tool of claim 1, wherein one end tapers in thickness from the point where it connects to the curved section to the first corner.

16. The dental tool of claim 15, wherein the one end has a thickness at the connection at the curved section in a range of 1-2 mm, and a thickness at the first corner in a range of 0.1-1 mm.

17. A method for restoring a tooth, comprising:
    filling a tooth cavity with a dental restoration;
    compressing and/or distributing the dental restoration with the dental tool of claim 1 thereby shaping the dental restoration to conform to a shape of the tooth; and
    removing excess dental restoration.

18. The method of claim 17, wherein the dental restoration is an uncured composite resin.

* * * * *